(12) United States Patent
Murakami et al.

(10) Patent No.: US 8,773,159 B2
(45) Date of Patent: Jul. 8, 2014

(54) METHOD OF INSPECTING PRINTED CIRCUIT BOARD, METHOD OF MANUFACTURING PRINTED CIRCUIT BOARD AND INSPECTION DEVICE OF PRINTED CIRCUIT BOARD

(75) Inventors: Kousuke Murakami, Ibaraki (JP); Yoshihiro Toyoda, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 365 days.

(21) Appl. No.: 12/908,984

(22) Filed: Oct. 21, 2010

(65) Prior Publication Data

US 2011/0095781 A1  Apr. 28, 2011

(30) Foreign Application Priority Data

Oct. 27, 2009 (JP) ................................ 2009-246674

(51) Int. Cl.
*G01R 31/28* (2006.01)

(52) U.S. Cl.
USPC . 324/763.01; 324/537; 324/538; 324/761.01; 382/148; 382/150; 29/741; 29/743; 29/832; 438/795

(58) Field of Classification Search
USPC .............. 324/537, 538, 761, 763; 382/8, 148, 382/150; 356/237; 358/106; 29/741, 743, 29/832; 438/795; 174/261, 262, 88 R
See application file for complete search history.

(56) References Cited

U.S. PATENT DOCUMENTS

| | | | |
|---|---|---|---|
| 6,240,633 B1 * | 6/2001 | Kent et al. ....................... | 29/832 |
| 6,407,345 B1 * | 6/2002 | Hirose et al. .................. | 174/261 |
| 6,667,250 B2 * | 12/2003 | Sasaoka et al. ............... | 438/795 |
| 7,757,626 B2 * | 7/2010 | Shinya et al. .................. | 118/101 |
| 2009/0113704 A1 | 5/2009 | Toyoda | |
| 2010/0027873 A1 | 2/2010 | Kakuda | |

FOREIGN PATENT DOCUMENTS

| | | | | |
|---|---|---|---|---|
| CN | 1469171 A | | 1/2004 | |
| CN | 101426339 A | | 5/2009 | |
| CN | 101512325 A | | 8/2009 | |
| JP | 02-068667 A | | 3/1990 | |
| JP | 2001-228091 A | | 8/2001 | |
| JP | 2002076569 A | * | 3/2002 | ............... H05K 3/00 |

OTHER PUBLICATIONS

Office Action issued Nov. 4, 2013 in CN Application No. 201010527718.8.

* cited by examiner

*Primary Examiner* — Patrick Assouad
*Assistant Examiner* — Sean Curtis
(74) *Attorney, Agent, or Firm* — Panitch Schwarze Belisario & Nadel LLP

(57) ABSTRACT

A plurality of assembly sheets are placed on an upper surface of a substrate adsorption platform, and a pressing plate is placed on the plurality of assembly sheets placed on the substrate adsorption platform such that the plurality of assembly sheets are pressed by the pressing plate. In this state, a DC power supply device is turned on and causes the upper surface of the substrate adsorption platform to be charged, thereby causing the plurality of assembly sheets to be adsorbed on the upper surface by an electrostatic force. Then, the pressing plate placed on the plurality of assembly sheets is removed while the upper surface of the substrate adsorption platform is charged, and automatic appearance inspection is performed on the plurality of assembly sheets adsorbed on the upper surface of the substrate adsorption platform.

6 Claims, 9 Drawing Sheets

F I G. 7
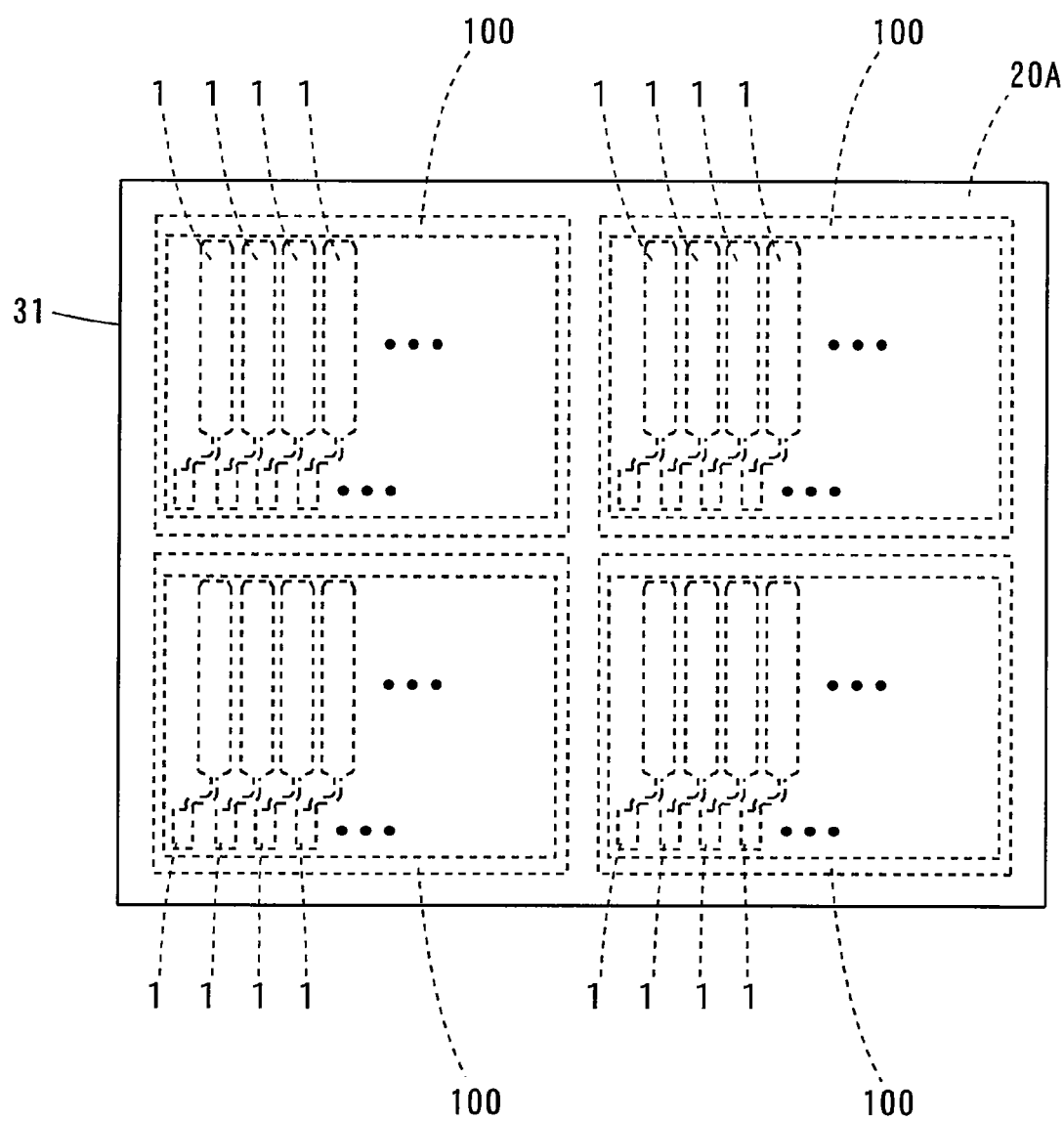

F I G. 9
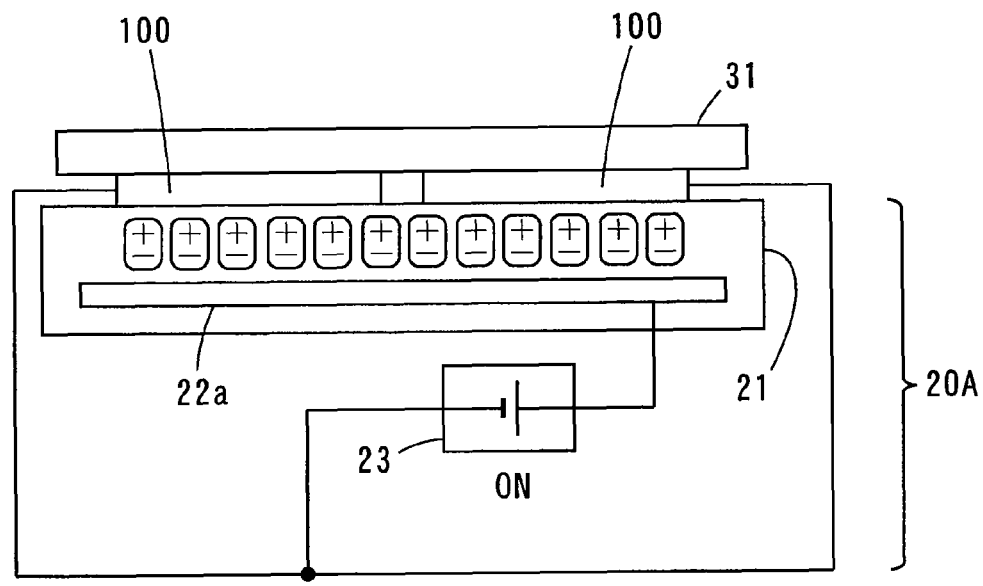

METHOD OF INSPECTING PRINTED CIRCUIT BOARD, METHOD OF MANUFACTURING PRINTED CIRCUIT BOARD AND INSPECTION DEVICE OF PRINTED CIRCUIT BOARD

BACKGROUND OF THE INVENTION

1. Field of the Invention

The present invention relates to a method of inspecting a printed circuit board, a method of manufacturing a printed circuit board and an inspection device of a printed circuit board.

2. Description of the Background Art

Electronic apparatuses such as hard disk drives or cellular telephones are provided with printed circuit boards having conductor traces formed thereon. Sometimes, automatic appearance inspection such as AVI (Automatic Visual Inspection) is performed in manufacture of such printed circuit boards.

In the AVI, the presence/absence of defective pieces having defects in conductor traces, dimensional errors of conductor traces, defects in terminals and damaged resist surfaces and so on can be determined in a short period of time in the final stage of manufacturing steps of the printed circuit boards.

The AVI is performed in the following manner, for example. First, a good printed circuit board with no defect is imaged by an imaging device, and obtained image data is stored in a memory as master data. Then, a printed circuit board to be inspected is imaged by the imaging device, and obtained image data is stored in the memory as inspection target data. The master data and the inspection target data are subsequently compared with each other, so that determination as to whether or not the printed circuit board is defective is made.

In the AVI, since the determination as to whether or not the printed circuit board is defective is made based on the image data, the printed circuit board must be reliably fixed when being imaged. Therefore, an AVI device is provided with an inspection platform including a holding mechanism that holds the printed circuit board. Examples of the holding mechanism include a clamp mechanism, a vacuum suction mechanism and an electrostatic adsorption mechanism.

In an inspection platform including the clamp mechanism (hereinafter referred to as a clamp inspection platform), ends of the printed circuit board are fixed on the inspection platform by a plurality of clamps while the printed circuit board is placed on the inspection platform.

An inspection platform including the vacuum suction mechanism (hereinafter referred to as a vacuum inspection platform) has a through hole that penetrates the inspection platform from its upper surface to its lower surface, for example. In addition, a suction device that sucks in an atmosphere above the upper surface of the inspection platform through the through hole is provided on a lower surface side of the inspection platform. The suction device is operated while the printed circuit board is placed on the inspection platform, so that the printed circuit board is attracted through the through hole by the suction device to be fixed on the inspection platform.

An inspection platform including the electrostatic adsorption mechanism (hereinafter referred to as an electrostatic inspection platform) includes an insulator that forms an upper surface of the inspection platform, for example. An electrical conductor is provided below the insulator. The electrical conductor is composed of a positive electrode plate and a negative electrode plate each arranged in parallel with the upper surface of the inspection platform. Voltage is applied between the positive electrode plate and the negative electrode plate of the electrical conductor while the printed circuit board is placed on the inspection platform, so that the insulator polarizes to induce positive charges and negative charges on the upper surface of the inspection platform. Thus, an electrostatic force (Coulomb force) arising from the induced positive charges and negative charges causes the printed circuit board to be adsorbed on the upper surface of the inspection platform to be fixed on the inspection platform.

Since the ends of the printed circuit board are fixed by the plurality of clamps in the above-described clamp inspection platform, a tensile force is exerted between the plurality of ends of the printed circuit board. Therefore, the printed circuit board may be fixed on the inspection platform while having wrinkles generated thereon. In this case, it is difficult to perform accurate AVI.

If a number of holes are formed in the printed circuit board, the printed circuit board cannot be adsorbed on the inspection platform in some cases in the vacuum inspection platform. In addition, a suction force is locally generated in the portion where the through hole is formed in the inspection platform. Therefore, an uneven suction force is exerted on the printed circuit board, thereby causing strain in the printed circuit board in some cases. Also in this case, it is difficult to perform accurate AVI.

In the electrostatic inspection platform, since the object is adsorbed by the electrostatic force, a sufficient adsorption force cannot be obtained in a case where the printed circuit board and the upper surface of the inspection platform are not in close proximity to each other. Therefore, the printed circuit board cannot be adsorbed on the upper surface of the inspection platform when strain such as warp occurs in the printed circuit board. In this case, it is difficult to perform accurate AVI.

JP 2002-76569 A describes an inspection device of a printed board using the electrostatic inspection platform. In the inspection device, the printed board is pressed against the upper surface of the inspection platform by a squeeze roller while being electrostatically adsorbed on the inspection platform. This causes the printed board to be flattened on the inspection platform.

In fact, however, a frictional force or the like occurs between the printed board and the squeeze roller, causing wrinkles in the printed board in some cases. In addition, the surface of the squeeze roller is adhesive. Therefore, when the printed board happens to stick to the squeeze roller, it may be raised from the inspection platform as the squeeze roller moves. Also in these cases, it is difficult to perform accurate AVI.

BRIEF SUMMARY OF THE INVENTION

An object of the present invention is to provide a method of inspecting a printed circuit board, a method of manufacturing a printed circuit board and an inspection device of a printed circuit board that allow for accurate automatic appearance inspection.

(1) According to an aspect of the present invention, a method of inspecting a printed circuit board includes the steps of placing the printed circuit board on a support surface of an adsorption platform, placing a pressing member on the printed circuit board placed on the support surface such that the printed circuit board is pressed by an insulating pressing surface of the pressing member, adsorbing the printed circuit board on the support surface by an electrostatic force by charging the support surface while the printed circuit board and the pressing member are placed on the support surface, removing the pressing member placed on the printed circuit board while the support surface is charged, and performing automatic appearance inspection on the printed circuit board adsorbed on the support surface.

In the inspecting method, the printed circuit board is placed on the support surface of the adsorption platform, and the pressing member is placed on the printed circuit board placed on the support surface such that the printed circuit board is pressed by the insulating pressing surface of the pressing member. Thus, the entire surface of the printed circuit board is uniformly pressed by the pressing member, so that the printed circuit board uniformly comes in contact with the support surface of the adsorption platform while being flattened.

The support surface of the adsorption platform is charged in this state, thereby causing the printed circuit board to be adsorbed on the support surface by an electrostatic force. This causes the printed circuit board to be fixed in a flattened state on the support surface.

Then, the pressing member placed on the printed circuit board is removed while the support surface is charged, and the automatic appearance inspection is performed on the printed circuit board adsorbed on the support surface. Accordingly, the automatic appearance inspection can be accurately performed while the flattened printed circuit board is reliably fixed on the support surface of the adsorption platform.

(2) The pressing surface of the pressing member may be formed of insulating glass or insulating resin. The pressing surface of the pressing member is formed of the insulating material, thereby reliably preventing discharge from being generated between the support surface and the pressing member.

The insulating glass or the insulating resin easily becomes charged. Therefore, if the support surface is charged with the printed circuit board and the pressing member placed thereon, the pressing member also becomes charged in some cases. In this case, the pressing surface of the pressing member becomes charged, so that foreign matters on the printed circuit board are adsorbed on the pressing surface of the pressing member by an electrostatic force. Accordingly, the foreign matters on the printed circuit board are adsorbed on the pressing surface to be removed from the printed circuit board when the pressing member is removed from the support surface.

(3) The resin may include at least one of polyvinyl chloride, acrylic resin, polycarbonate and polytetrafluoroethylene.

Polyvinyl chloride, acrylic resin, polycarbonate and polytetrafluoroethylene are insulating materials that are easily charged. Thus, discharge can be reliably prevented from being generated between the support surface of the adsorption platform and the pressing surface of the pressing member, and foreign matters on the printed circuit board can be reliably removed.

(4) The pressing member may be formed of a material having light transmission properties.

In this case, the printed circuit board can be seen through the pressing member when the pressing member is placed on the printed circuit board placed on the support surface, thus allowing for confirmation as to whether or not the printed circuit board is accurately positioned on the support surface.

(5) According to another aspect of the present invention, a method of manufacturing a printed circuit board includes the steps of preparing the printed circuit board before inspection by forming a conductor trace on an insulating layer, placing the printed circuit board before inspection on a support surface of an adsorption platform, placing a pressing member on the printed circuit board before inspection placed on the support surface such that the printed circuit board before inspection is pressed by an insulating pressing surface of the pressing member, adsorbing the printed circuit board before inspection on the support surface by an electrostatic force by charging the support surface while the printed circuit board before inspection and the pressing member are placed on the support surface, removing the pressing member placed on the printed circuit board before inspection while the support surface is charged, and performing automatic appearance inspection on the printed circuit board before inspection adsorbed on the support surface.

In the manufacturing method, the printed circuit board before inspection is prepared by forming the conductor trace on the insulating layer, and the prepared printed circuit board before inspection is placed on the support surface of the adsorption platform. The pressing member is placed on the printed circuit board before inspection placed on the support surface such that the printed circuit board before inspection is pressed by the insulating pressing surface of the pressing member. Thus, the entire surface of the printed circuit board before inspection is uniformly pressed by the pressing member, so that the printed circuit board before inspection uniformly comes in contact with the support surface of the adsorption platform while being flattened.

The support surface of the adsorption platform becomes charged in this state, thereby causing the printed circuit board before inspection to be adsorbed on the support surface by an electrostatic force. This causes the printed circuit board before inspection to be fixed in a flattened state on the support surface.

Then, the pressing member placed on the printed circuit board before inspection is removed while the support surface is charged, and the automatic appearance inspection is performed on the printed circuit board adsorbed on the support surface. Accordingly, the automatic appearance inspection can be accurately performed while the flattened printed circuit board before inspection is reliably fixed on the support surface of the adsorption platform. This allows for accurate determination as to whether or not the printed circuit board is defective.

(6) According to still another aspect of the present invention, an inspection device of a printed circuit board includes an adsorption platform that has a support surface on which the printed circuit board is placed, and is configured such that the support surface can be switched between a charged state and an uncharged state, a pressing member that has an insulating pressing surface, a moving device arranged to move the pressing member, a detection device arranged to perform automatic appearance inspection on the printed circuit board placed on the support surface of the adsorption platform, and a controller arranged to control operations of the adsorption platform, the moving device and the detection device, wherein the controller controls the moving device to place the pressing member on the printed circuit board such that the printed circuit board is pressed by the pressing surface while the printed circuit board is placed on the support surface of the adsorption platform, switches the support surface of the adsorption platform to the charged state while the printed circuit board and the pressing member are placed on the support surface to cause the printed circuit board to be adsorbed on the support surface by an electrostatic force, controls the moving device to remove the pressing member placed on the printed circuit board in the charged state of the support surface, and controls the detection device to perform automatic appearance inspection on the printed circuit board adsorbed on the support surface.

With the printed circuit board placed on the support surface of the adsorption platform, the pressing member is placed on the printed circuit board placed on the support surface by the moving device such that the printed circuit board is pressed by the insulating pressing surface of the pressing member in the inspection device. Thus, the entire surface of the printed circuit board is uniformly pressed by the pressing member, so that the printed circuit board uniformly comes in contact with the support surface of the adsorption platform while being flattened.

In this state, the support surface of the adsorption platform is switched to the charged state, thereby causing the printed circuit board to be adsorbed on the support surface by an electrostatic force. This causes the printed circuit board to be fixed in a flattened state on the support surface.

Then, the pressing member placed on the printed circuit board is removed by the moving device while the support surface is charged, and the detecting device performs the automatic appearance inspection on the printed circuit board adsorbed on the support surface. Accordingly, accurate automatic appearance inspection can be performed while the flattened printed circuit board is reliably fixed on the support surface of the adsorption platform.

Other features, elements, characteristics, and advantages of the present invention will become more apparent from the following description of preferred embodiments of the present invention with reference to the attached drawings.

BRIEF DESCRIPTION OF THE SEVERAL VIEWS OF THE DRAWINGS

FIG. 2 (b) is a sectional view of the suspension board of FIG. 1 taken along the line B-B.

FIG. 7 is a plane view of a substrate adsorption platform on which a pressing plate of FIG. 5 is placed.

FIG. 9 is a block diagram showing another example of the configuration of the substrate adsorption platform.

DETAILED DESCRIPTION OF THE INVENTION

Figure 1:
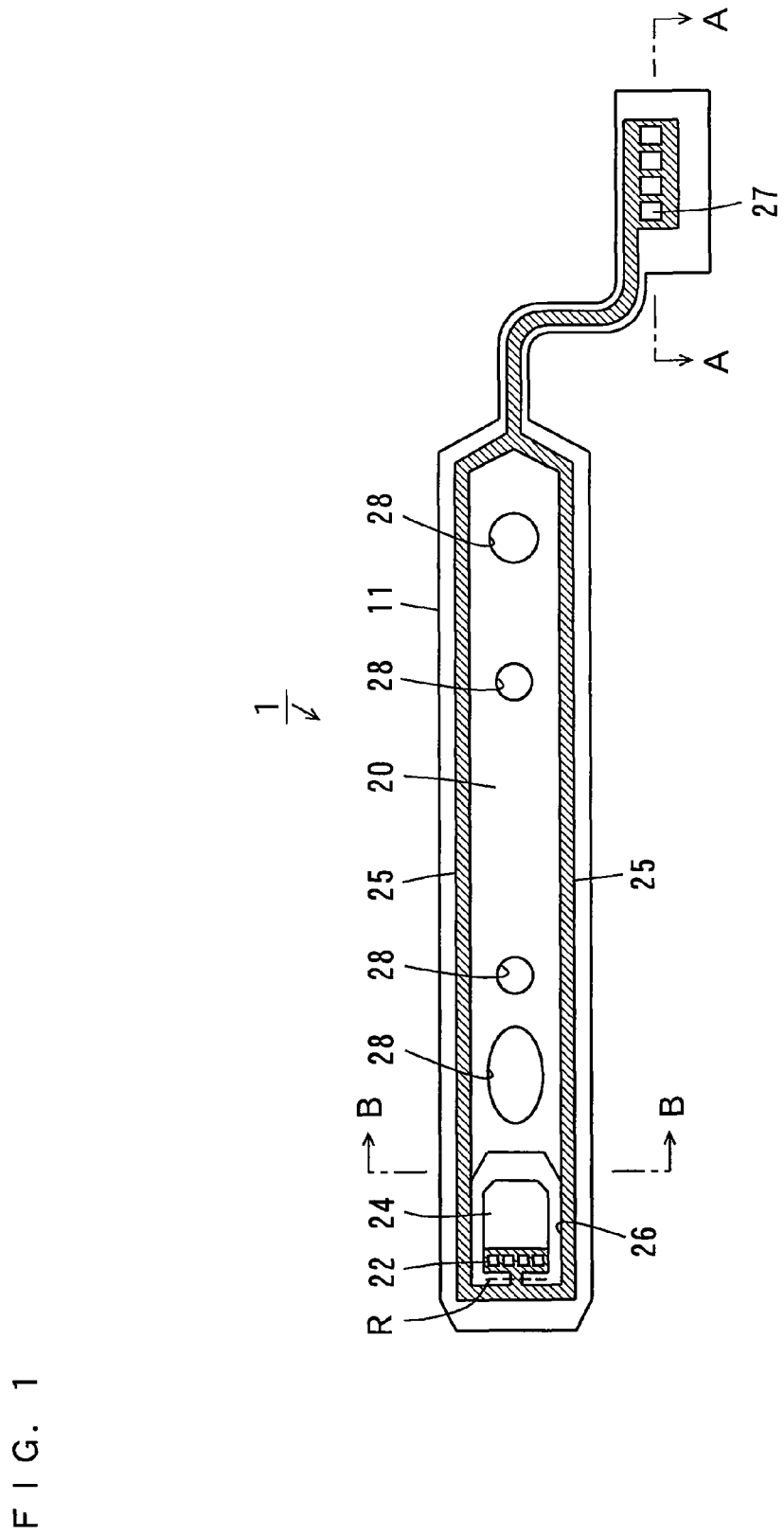
FIG. 1 is a plane view of a suspension board.

Hereinafter, description will be made of a method of inspecting a printed circuit board, a method of manufacturing a printed circuit board and an inspection device of a printed circuit board according to an embodiment of the present invention while referring to the drawings. The method of inspecting the printed circuit board and the inspection device of the printed circuit board according to the present embodiment are used in an automatic appearance inspecting step for determining whether or not a suspension board with circuits (hereinafter abbreviated as a suspension board) is defective in manufacture of the suspension board described below, for example. The automatic appearance inspection includes AVI (Automatic Visual Inspection) and AOI (Automatic Optical Inspection), for example. First, description is made of the configuration of the suspension board to be inspected.

(1) CONFIGURATION OF THE SUSPENSION BOARD

Figure 2:
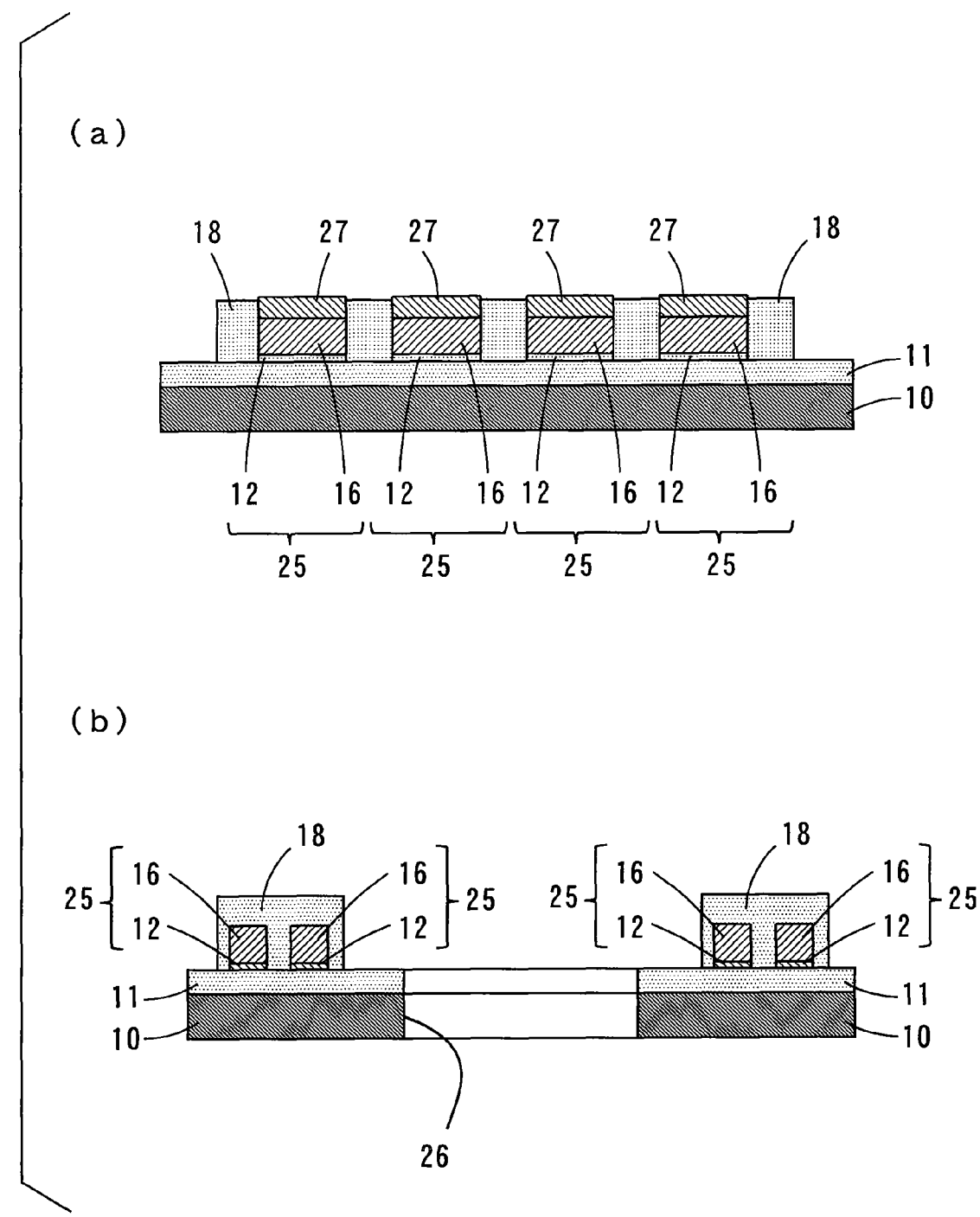
FIG. 2 (a) is a sectional view of the suspension board of FIG. 1 taken along the line A-A.

FIG. 1 is a plane view of the suspension board. FIG. 2 (a) and (b) are sectional views of the suspension board of FIG. 1 taken along the line A-A and the line B-B, respectively.

As shown in FIG. 1, the suspension board 1 includes a suspension body 20 formed of a support substrate 10 (see FIG. 2), described below, and an insulating layer 11. Conductor traces 25 are formed on the suspension body 20. The conductor traces 25 are schematically indicated by hatching in FIG. 1. At the tip of the suspension body 20, a U-shaped opening 26 is formed, thereby providing a magnetic head supporting portion (hereinafter referred to as a tongue) 24. The tongue 24 is bent along the broken line R to form a given angle with respect to the suspension body 20.

Four electrode pads 22 are formed at an end of the tongue 24. Four electrode pads 27 are formed at the other tip of the suspension body 20. The electrode pads 22 on the tongue 24 and the electrode pads 27 at the other tip of the suspension body 20 are electrically connected to one another through the conductor traces 25. A plurality of holes 28 are formed in the suspension body 20. A cover layer 18 (see FIG. 2), described below, is not shown in FIG. 1.

As shown in FIG. 2 (a), the insulating layer 11 made of polyimide is formed on the support substrate 10 made of stainless steel in the cross section taken along the line A-A of FIG. 1. A chromium film 12 and a conductor layer 16 that is made of copper are sequentially stacked at four positions on the insulating layer 11, and an electrode pad 27 made of gold is formed on each of the conductor layers 16. An upper surface of the insulating layer 11 is covered with the cover layer 18 made of polyimide with upper surfaces of the electrode pads 27 uncovered.

As shown in FIG. 2 (b), the insulating layer 11 made of polyimide is formed on the support substrate 10 made of stainless steel also in the cross section taken along the line B-B of FIG. 1. The chromium film 12 and the conductor layer 16 that is made of copper are sequentially stacked at respective two positions on one side portion and the other side portion of the insulating layer 11. The two sets of chromium film 12 and conductor layer 16 on each side portion are covered with the cover layer 18 made of polyimide. Traces each composed of the chromium film 12 and the conductor layer 16 constitute the conductor traces 25.

(2) MANUFACTURE OF THE SUSPENSION BOARD

Figure 3:
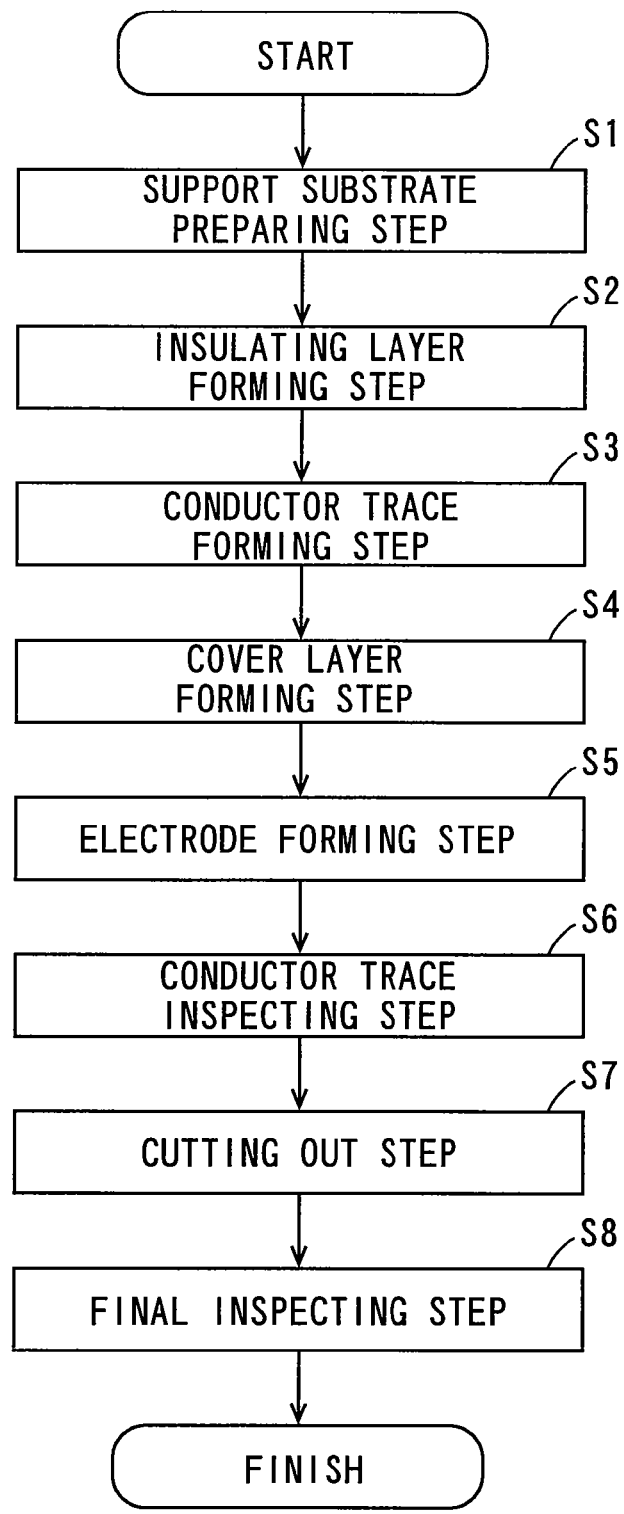
FIG. 3 is a schematic flowchart showing steps of manufacturing the suspension board of FIG. 1.

The foregoing suspension board 1 is prepared as follows, for example. In the manufacturing processes of the suspension board 1, an assembly sheet on which the plurality of suspension boards 1 are integrally formed is prepared as a half-finished product. Details of the assembly sheet will be described below. FIG. 3 is a schematic flowchart showing steps of manufacturing the suspension board 1 of FIG. 1.

First, a long-sized support substrate 10 is prepared as mentioned in FIG. 3 (a support substrate preparing step: Step S1). A stainless steel plate, for example, can be used as the support substrate 10. Here, a plurality of regions of the support substrate 10 corresponding to the plurality of suspension boards 1 are referred to as substrate regions.

Next, the insulating layer 11 is integrally formed on one surface of the prepared support substrate 10 (an insulating layer forming step: Step S2). The conductor traces 25 each composed of the chromium film 12 and the conductor layer 16 are formed on the insulating layer 11 (a conductor trace forming step: Step S3). Here, the plurality of conductor traces 25 of FIG. 1 are formed on each of the plurality of substrate regions of the support substrate 10. The conductor traces 25 may be formed using an additive method or a semi-additive method, for example. Alternatively, another method such as a subtractive method may be used.

Then, the cover layer 18 (see FIG. 2) made of polyimide having a given pattern is formed on the insulating layer 11 and the conductor traces 25 (a cover layer forming step: Step S4).

With the cover layer 18 formed, the four electrode pads 22 and the four electrode pads 27 are formed on the positions of the conductor traces 25 corresponding to the tongue 24 and the other tip of the suspension body 20 of FIG. 1, respectively (an electrode forming step: Step S5).

Next, continuity check, AOI and visual check are sequentially performed in order to detect defects in the conductor traces 25 formed in the plurality of substrate regions (a conductor trace inspecting step: Step S6).

In the continuity check, electrical continuity of the conductor traces 25 formed on each substrate region is inspected. In the AOI, image data obtained by imaging good conductor traces 25 with no defect is compared with image data obtained by imaging the conductor traces 25 to be inspected, thereby detecting defects in the conductor traces 25 to be inspected. After the continuity check and the AOI, a worker visually checks using a microscope positions in which defects are detected through the AOI. Accordingly, defects in the conductor traces 25 are reliably detected.

Then, given regions of the support substrate 10 excluding the plurality of substrate regions are cut out (a cutting out step: Step S7). In this manner, the assembly sheet in which the plurality of suspension boards 1 are integrally formed is completed.

Figure 4:
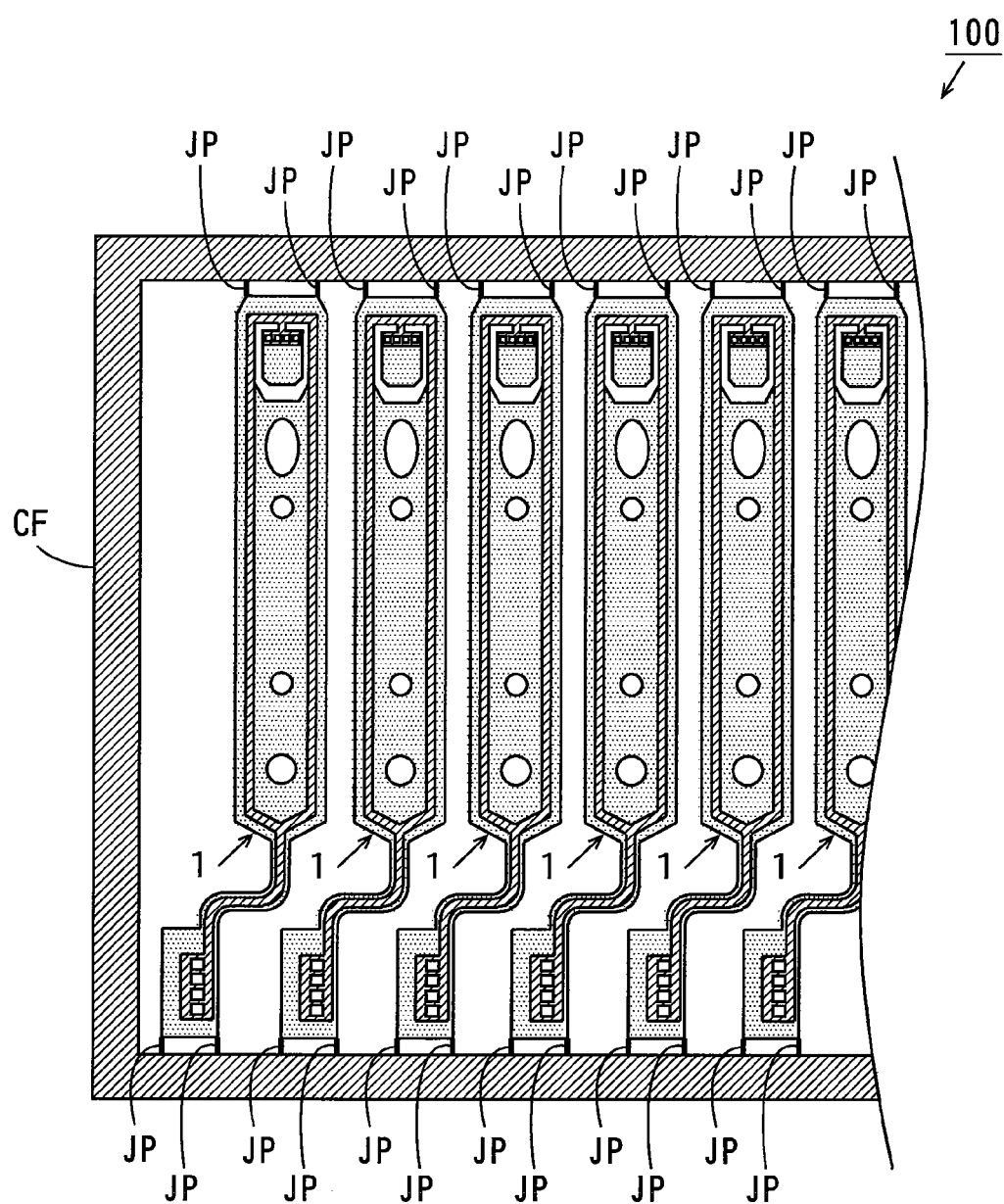
FIG. 4 is a partially enlarged plane view showing an assembly sheet after a cutting out step.

FIG. 4 is a partially enlarged plane view showing the assembly sheet after the cutting out step. As shown in FIG. 4, the plurality of suspension boards 1 are arranged along one direction within a substantially rectangular frame CF in the assembly sheet 100. Coupling portions JP that couple the frame CF and each suspension board 1 are formed inside the frame CF.

Returning to FIG. 3, finally, the AVI is performed for determining whether or not each suspension board 1 of the assembly sheet 100 is defective (a final inspecting step: Step S8). In the AVI, determination as to whether or not the plurality of suspension boards 1 prepared through the foregoing Steps S1 to S7 have defects in the conductor traces, dimensional errors of the conductor traces, defects in terminals, damages on resist surfaces and so on is made in a short period of time. Details will be described below.

The suspension boards 1 that are not determined to be defective in the AVI are removed from the frame CF by cutting off the coupling portions JP and shipped as acceptable products (good products).

(3) CONFIGURATION OF AVI DEVICE

Figure 5:
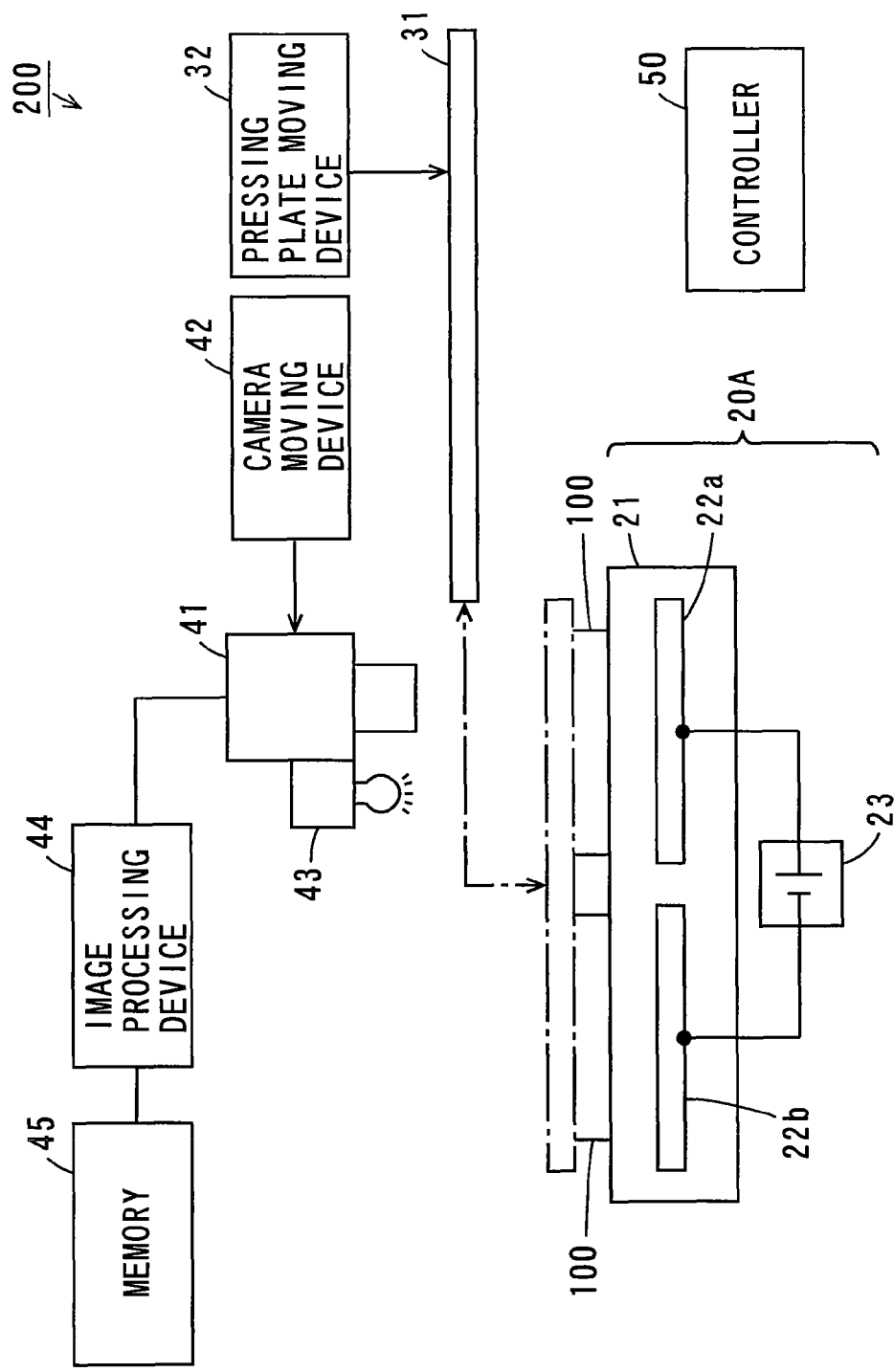
FIG. 5 is a block diagram showing one example of the configuration of an AVI device used in a final inspecting step of FIG. 3.

The AVI in the final inspecting step of FIG. 3 is performed using an AVI device described below. FIG. 5 is a block diagram showing one example of the configuration of the AVI device used in the final inspecting step of FIG. 3.

As shown in FIG. 5, the AVI device 200 includes a substrate adsorption platform 20A, a pressing plate 31, a pressing plate moving device 32, a CCD (Charge Coupled Device) camera 41, a camera moving device 42, a light source 43, an image processing device 44, a memory 45 and a controller 50.

The substrate adsorption platform 20A is a bipolar electrostatic adsorption platform that adsorbs an object (the assembly sheet 100 in this example) by an electrostatic force. The substrate adsorption platform 20A includes an insulator 21, a positive plate 22a, a negative plate 22b and a DC power supply device 23.

The insulator 21 is formed of an insulating material such as ceramic, and forms an upper surface of the substrate adsorption platform 20A, that is, a surface on which the assembly sheets 100 are placed. In the present embodiment, the upper surface of the substrate adsorption platform 20A is formed such that its length and width measurement are each 350 mm, for example. Surface roughness, which is surface roughness (Ra) based on JIS (Japanese Industrial Standards) B 0601, of the insulator 21 is preferably not more than 10 μm, for example, in the upper surface of the substrate adsorption platform 20A.

The positive plate 22a and the negative plate 22b are each formed of an electrically conductive material such as copper, for example, and are arranged adjacent to each other in positions spaced apart from the upper surface of the insulator 21 inside the insulator 21. The positive plate 22a is connected to a positive terminal of the DC power supply device 23. The negative plate 22b is connected to a negative terminal of the DC power supply device 23.

When the DC power supply device 23 is turned on, a voltage is applied between the positive plate 22a and the negative plate 22b. This causes the insulator 21 to polarize, resulting in induction of positive charges and negative charges in the upper surface of the substrate adsorption platform 20A, as will be described below. Accordingly, an electrostatic force arising from the induced positive charges and negative charges works as an adsorption force between the substrate adsorption platform 20A, described below, and the assembly sheets 100. On the other hand, a voltage is not applied between the positive plate 22a and the negative plate 22b when the DC power supply device 23 is turned off. Thus, the electrostatic force is not generated in the upper surface of the substrate adsorption platform 20A. Details of an operation of the substrate adsorption platform 20A will be described below.

As indicated by the one-dot and dash line in FIG. 5, the pressing plate moving device 32 supports the pressing plate 31 in a movable manner between a position above the substrate adsorption platform 20A and a position beside the substrate adsorption platform 20A.

The pressing plate 31 is formed of an insulating material. A material that is easily charged is preferably used as the insulating material for the pressing plate 31. In this case, glass or resin such as polyvinyl chloride, acrylic resin, polycarbonate or polytetrafluoroethylene, for example, can be used as the pressing plate 31.

In the present embodiment, the pressing plate 31 is formed such that its length and width measurements are each 350 mm and its thickness is 10 mm, for example, similarly to the upper surface of the substrate adsorption platform 20A. The pressing plate 31 preferably has weight of 10 kg/m$^2$ or more.

The CCD camera 41 is provided above the substrate adsorption platform 20A. The CCD camera 41 is supported by the camera moving device 42 in a horizontally movable manner in a region above the upper surface of the substrate adsorption platform 20A.

The CCD camera 41 is provided with the light source 43. The image processing device 44 and the memory 45 are connected to the CCD camera 41.

The controller 50 of the AVI device 200 is composed of a CPU (Central Processing Unit) and a memory or composed of a microcomputer, for example, and controls operations of components of the AVI device 200.

(4) OPERATION OF THE AVI DEVICE

Figure 6:
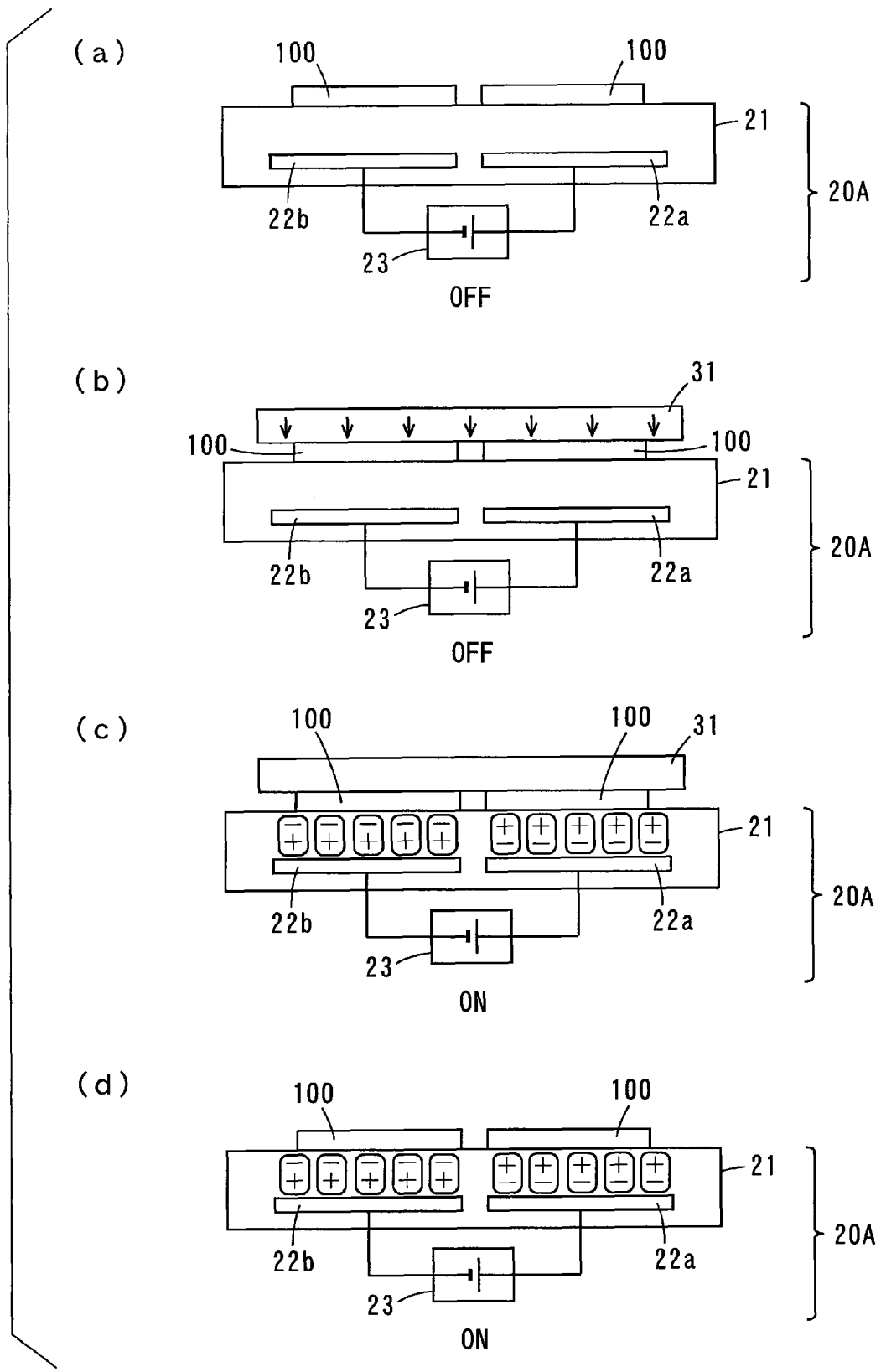
FIG. 6 is a diagram for explaining an operation of the AVI device at the time of AVI in the final inspecting step of FIG. 3.

FIG. 6 is a diagram for explaining an operation of the AVI device at the time of the AVI in the final inspecting step of FIG. 3. FIG. 6 (a) to (d) show schematic side views of the substrate adsorption platform 20A in the AVI device 200.

As shown in FIG. 6 (a), the plurality of assembly sheets 100 are placed on the substrate adsorption platform 20A such that the surfaces of the conductor traces 25 face the CCD camera 41. In this case, the plurality of assembly sheets 100 to be inspected are placed on the substrate adsorption platform 20A while being manually positioned by a worker, for example. The plurality of assembly sheets 100 may be placed on the substrate adsorption platform 20A by a transport device for the assembly sheets 100.

Next, the controller 50 controls the pressing plate moving device 32 to place the pressing plate 31 on the upper surface of the substrate adsorption platform 20A as shown in FIG. 6 (b). At this time, the DC power supply device 23 of the substrate adsorption platform 20A is maintained in an OFF state.

FIG. 7 is a plane view of the substrate adsorption platform 20A on which the pressing plate 31 of FIG. 5 is placed. In the example of FIG. 7, the pressing plate 31 is placed on the upper surface of the substrate adsorption platform 20A to cover the entire four assembly sheets 100 while the assembly sheets 100 are placed on the upper surface of the substrate adsorption platform 20A.

This causes the plurality of assembly sheets 100 on the substrate adsorption platform 20A to be pressed against the upper surface of the substrate adsorption platform 20A by the pressing plate 31. As a result, a uniform pressing force is exerted on the entire surfaces of the plurality of assembly sheets 100 (see the arrows in FIG. 6 (b)).

At this time, since the DC power supply device 23 is turned off, an adsorption force arising from the electrostatic force is not generated in the upper surface of the substrate adsorption platform 20A. Therefore, each assembly sheet 100 is easily flattened on the upper surface of the substrate adsorption platform 20A by the pressing force of the pressing palate 31.

Here, a material having high light transmission properties (light transmittance is 80% or more in a wavelength region including at least part of a wavelength region of visible light, for example) is preferably used as the pressing plate 31. This allows for confirmation as to whether or not the assembly sheets 100 are accurately positioned on the substrate adsorption platform 20A when being pressed.

Then, the DC power supply device 23 is switched from the OFF state to an ON state by the controller 50 as shown in FIG. 6 (c). At this time, an electric field is generated between the positive plate 22a and the negative plate 22b to cause the insulator 21 covering the upper surfaces of the positive plate 22a and the negative plate 22b to polarize.

In this case, positive charges are induced in a portion of the upper surface of the insulator 21 above the positive plate 22a, and negative charges are induced in a portion of the upper surface of the insulator 21 above the negative plate 22b. This causes an electrostatic force (Coulomb force) arising from the induced positive charges and negative charges to be generated between the upper surface of the substrate adsorption platform 20A and the conductor portions (the support substrates 10 and the conductor traces 25 each formed of the electrically conductive materials, for example) of the assembly sheets 100. The generated electrostatic force works as an adsorption force between the substrate adsorption platform 20A and the assembly sheets 100. As a result, the plurality of assembly sheets 100 are held by adsorption on the upper surface of the substrate adsorption platform 20A while being flattened.

After that, with the DC power supply device 23 maintained in the ON state, the controller 50 controls the pressing plate moving device 32 to outwardly move the pressing plate 31 from the position above the upper surface of the substrate adsorption platform 20A as shown in FIG. 6 (d).

Thus, the upper surfaces of the assembly sheets 100 are exposed while the plurality of flattened assembly sheets 100 are held by adsorption on the upper surface of the substrate adsorption platform 20A.

In this state, the controller 50 controls the camera moving device 42 to move the CCD camera 41 above the substrate adsorption platform 20A. At this time, the light source 43 emits light to cause the plurality of suspension boards 1 of the plurality of assembly sheets 100 to be irradiated with light having a given wavelength. Then, reflected light from each suspension board 1 is imaged by the CCD camera 41.

The image processing device 44 processes image data obtained by the CCD camera 41 based on predetermined image processing conditions. The processed image data is subsequently stored in the memory 45 as inspection target data.

Before the AVI is started, a good suspension board 1 with no defect is previously imaged by the CCD camera 41, obtained image data is processed based on the predetermined image processing conditions, and the processed image data is stored in the memory 45 as master data.

In the AVI, the controller 50 compares the inspection target data with the master data stored in the memory 45, and determines the presence/absence of defects in each suspension board 1.

Finally, all the suspension boards 1 on the substrate adsorption platform 20A are imaged, so that the DC power supply device 23 is switched from the ON state to the OFF state. This removes the adsorption force between the substrate adsorption platform 20A and the assembly sheets 100, and the assembly sheets are recovered.

As described above, the pressing plate 31 is formed of the insulating material. The reason is described below.

In the AVI, the assembly sheets 100 and the pressing plate 31 are placed on the substrate adsorption platform 20A, and the pressing plate 31 is removed while the DC power supply device 23 is maintained in the ON state. At this time, electric discharge may be induced between the pressing plate 31 and the upper surface of the substrate adsorption platform 20A if the pressing plate 31 is formed of an electrically conductive material. This causes the suspension boards 1 on the substrate adsorption platform 20A to be damaged in some cases. Therefore, the pressing plate 31 is formed of the insulating material in the present embodiment.

(5) EFFECTS (a) In the present embodiment, the plurality of assembly sheets 100 are placed on the upper surface of the substrate adsorption platform 20A, and the pressing plate 31 is placed on the plurality of assembly sheets 100 placed on the substrate adsorption platform 20A such that the plurality of assembly sheets 100 are pressed by the pressing plate 31. Since the entire surfaces of the plurality of assembly sheets 100 are uniformly pressed by the pressing plate 31, the plurality of assembly sheets 100 uniformly come in contact with the upper surface of the substrate adsorption platform 20A while being flattened.

In this state, the DC power supply device 23 enters the ON state and the upper surface of the substrate adsorption platform 20A is charged, so that the plurality of assembly sheets 100 are adsorbed on the upper surface of the substrate adsorption platform 20A by the electrostatic force. Accordingly, the plurality of assembly sheets 100 are fixed on the upper surface of the substrate adsorption platform 20A while being flattened.

Then, the pressing plate 31 placed on the plurality of assembly sheets 100 is removed while the upper surface of the substrate adsorption platform 20A is charged, and the AVI is performed on the plurality of assembly sheets 100 adsorbed on the upper surface of the substrate adsorption platform 20A. This allows for the accurate AVI while the plurality of flattened assembly sheets 100 are reliably fixed on the upper surface of the substrate adsorption platform 20A.

While the pressing plate 31 is placed on the substrate adsorption platform 20A and removed from the substrate adsorption platform 20A by the pressing plate moving device 32 of FIG. 5 in the present embodiment, these operations may be manually performed by a worker.

(b) In the present embodiment, the pressing plate 31 is removed from the upper surface of the substrate adsorption platform 20A while the DC power supply device 23 is maintained in the ON state as described above. In this case, foreign matters such as particles can be removed from the upper surface of the assembly sheet 100 that is adsorbed on the substrate adsorption platform 20A. Details are described below.

Figure 8:
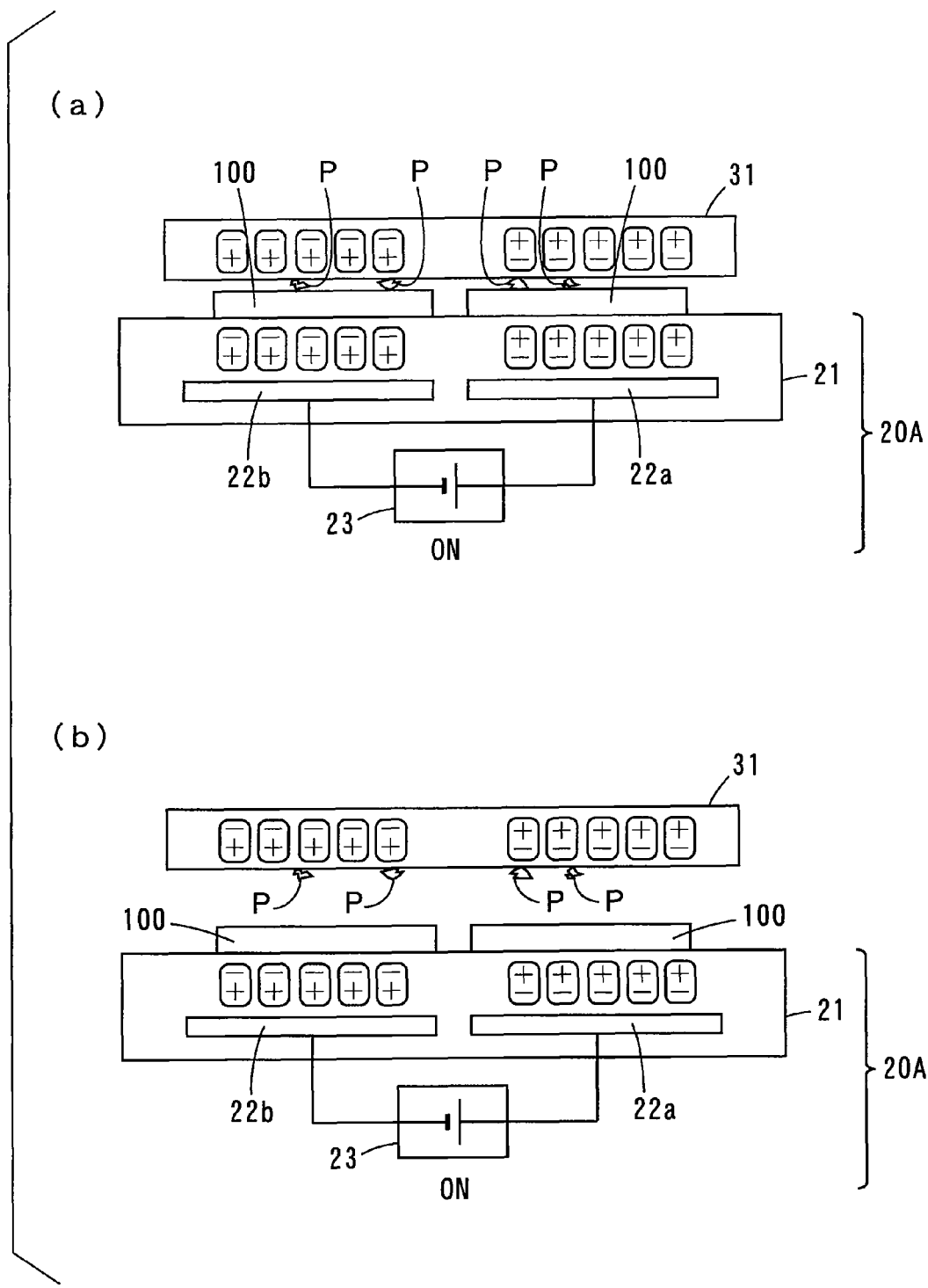
FIG. 8 is a diagram for explaining how foreign matters are removed from assembly sheets by the pressing plate of FIG. 5.

FIG. 8 is a diagram for explaining how foreign matters are removed from the assembly sheets 100 by the pressing plate 31 of FIG. 5. FIG. 8 (a), (b) each show a schematic side view of the substrate adsorption platform 20A in the AVI device 200.

In the present embodiment, the insulating material that is easily charged is used as the pressing plate 31. As shown in FIG. 8 (a), when the DC power supply device 23 enters the ON state while the plurality of assembly sheets 100 and the pressing plate 31 are placed on the upper surface of the substrate adsorption platform 20A, the positive charges are induced in the portion of the upper surface of the insulator 21 above the positive plate 22a and the negative charges are induced in the portion of the upper surface of the insulator 21 above the negative plate 22b as described above.

This generates electrostatic induction in the conductor portions of the plurality of assembly sheets 100. In the example of FIG. 8, positive charges are induced on an upper surface side of the assembly sheet 100 positioned above the positive plate 22a, and negative charges are induced on an upper surface side of the assembly sheet 100 positioned above the negative plate 22b.

This causes the pressing plate 31 covering the plurality of assembly sheets 100 to polarize. Specifically, negative charges are induced on a lower surface side of a portion of the pressing plate 31 positioned above the positive plate 22a, and positive charges are induced on a lower surface side of a portion of the pressing plate 31 positioned above the negative plate 22b.

Therefore, when foreign matters P exist on the upper surfaces of the assembly sheets 100, that is, between the assembly sheets 100 and the pressing plate 31, an electrostatic force that adsorbs the foreign matters P to a lower surface of the pressing plate 31 is generated.

As a result, when the pressing plate 31 is removed, the foreign matters P on the assembly sheets 100 are adsorbed to the lower surface of the pressing plate 31 to be removed from the upper surfaces of the assembly sheets 100 as shown in FIG. 8 (b).

(6) ANOTHER EXAMPLE OF THE CONFIGURATION OF THE SUBSTRATE ADSORPTION PLATFORM

A unipolar electrostatic adsorption platform including any of the positive plate 22a and the negative plate 22b inside the insulator 21 may be used instead of the bipolar substrate adsorption platform 20A of FIGS. 5 to 8.

FIG. 9 is a block diagram showing another example of the configuration of the substrate adsorption platform 20A. The substrate adsorption platform 20A of this example includes the insulator 21, the positive plate 22a and the DC power supply device 23. These components are the same as those in the substrate adsorption platform 20A of FIG. 5.

In the substrate adsorption platform 20A, the positive plate 22a is connected to the positive terminal of the DC power supply device 23. Then, each assembly sheet 100 on the substrate adsorption platform 20A is connected to the negative terminal of the DC power supply device 23.

When the DC power supply device 23 is turned on, a voltage is applied between the positive plate 22a and the negative plate 22b. This causes the insulator 21 to polarize, resulting in induction of positive charges in the upper surface of the substrate adsorption platform 20A, as will be described below. Accordingly, an electrostatic force arising from the induced positive charges works as an adsorption force between the substrate adsorption platform 20A, described below, and the assembly sheets 100. On the other hand, a voltage is not applied between the positive plate 22a and the negative plate 22b when the DC power supply device 23 is turned off. Thus, the electrostatic force is not generated in the upper surface of the substrate adsorption platform 20A. Details of an operation of the substrate adsorption platform 20A will be described below.

In this manner, the electrostatic force can be easily generated at desired timings in the substrate adsorption platform 20A by switching the DC power supply device 23 between the ON state and the OFF state in the unipolar electrostatic adsorption platform 20A of FIG. 9, similarly to the bipolar substrate adsorption platform 20A of FIGS. 5 to 8.

Accordingly, in the final inspecting step, the substrate adsorption platform 20A of this example provides the same effects as those described above.

(7) MODIFICATIONS

While the plate-shaped pressing plate 31 is used for pressing the plurality of assembly sheets 100 against the upper surface of the substrate adsorption platform 20A in the present embodiment, the present invention is not limited to this.

A configuration for pressing the plurality of assembly sheets 100 against the upper surface of the substrate adsorption platform 20A can be achieved by having an insulating pressing surface that presses the plurality of assembly sheets 100 against the upper surface of the substrate adsorption platform 20A. Therefore, a projection such as a pull may be formed on a surface on the opposite side of the pressing surface of the pressing plate 31, for example. Also in this case, the same effects as described above can be obtained.

(8) CORRESPONDENCES BETWEEN ELEMENTS IN THE CLAIMS AND PARTS IN EMBODIMENTS

In the following paragraphs, non-limiting examples of correspondences between various elements recited in the claims below and those described above with respect to various preferred embodiments of the present invention are explained.

In the foregoing embodiment, the assembly sheet 100 and the suspension board 1 are examples of a printed circuit board, the substrate adsorption platform 20A is an example of an adsorption platform, and the upper surface of the substrate adsorption platform 20A is an example of a support surface.

The pressing plate 31 is an example of a pressing member, the lower surface of the pressing plate 31 is an example of a pressing surface, and the pressing plate moving device 32 is an example of a moving device.

The CCD camera 41, the camera moving device 42, the image processing device 44, the memory 45 and the controller 50 are an example of a detection device.

As each of various elements recited in the claims, various other elements having configurations or functions described in the claims can be also used.

While preferred embodiments of the present invention have been described above, it is to be understood that variations and modifications will be apparent to those skilled in the art without departing the scope and spirit of the present invention. The scope of the present invention, therefore, is to be determined solely by the following claims.

We claim:

1. A method of inspecting a printed circuit board comprising the steps of:
    placing said printed circuit board on a flat uncharged support surface of an adsorption platform;
    after placing said printed circuit board on said support surface, placing a pressing member on said printed circuit board placed on said support surface such that an entire upper surface of said printed circuit board is pressed by a flat insulating pressing surface of said pressing member while said support surface is uncharged, and while said printed circuit board is not adsorbed on said support surface, wherein said pressing surface of said pressing member is configured to come into contact with the entire upper surface of said printed circuit board;
    after placing said pressing member on said printed circuit board, adsorbing said printed circuit board on said support surface by an electrostatic force by charging said support surface while said printed circuit board and said pressing member are placed on said support surface;
    after adsorbing said printed circuit board on said support surface, removing said pressing member placed on said printed circuit board while said support surface is charged; and
    after removing said pressing member, performing automatic appearance inspection on said printed circuit board adsorbed on said support surface.

2. The method of inspecting the printed circuit board according to claim 1, wherein said pressing surface of said pressing member is formed of insulating glass or insulating resin.

3. The method of inspecting the printed circuit board according to claim 2, wherein said resin includes at least one of polyvinyl chloride, acrylic resin, polycarbonate and polytetrafluoroethylene.

4. The method of inspecting the printed circuit board according to claim 1, wherein said pressing member is formed of a material having light transmission properties.

5. A method of manufacturing a printed circuit board, comprising the steps of:
    preparing the printed circuit board before inspection by forming a conductor trace on an insulating layer;
    placing said printed circuit board before inspection on a flat uncharged support surface of an adsorption platform;
    after placing said printed circuit board before inspection on said support surface, placing a pressing member on said printed circuit board before inspection placed on said support surface such that an entire upper surface of said printed circuit board before inspection is pressed by a flat insulating pressing surface of said pressing member while said support surface is uncharged, and while said printed circuit board is not adsorbed on said support surface, wherein said pressing surface of said pressing member is configured to come into contact with the entire upper surface of said printed circuit board;
    after placing said pressing member on said printed circuit board, adsorbing said printed circuit board before inspection on said support surface by an electrostatic force by charging said support surface while said printed circuit board before inspection and said pressing member are placed on said support surface;
    after adsorbing said printed circuit board on said support surface, removing said pressing member placed on said printed circuit board before inspection while said support surface is charged; and
    after removing said pressing member, performing automatic appearance inspection on said printed circuit board before inspection adsorbed on said support surface.

6. An inspection device of a printed circuit board comprising:
    an adsorption platform that has a flat support surface on which the printed circuit board is placed, and is configured such that said support surface can be switched between a charged state and an uncharged state;
    a pressing member that has a flat insulating pressing surface, wherein said pressing surface of said pressing member is configured to come into contact with an entire upper surface of said printed circuit board;
    a moving device arranged to move said pressing member;
    a detection device arranged to perform automatic appearance inspection on said printed circuit board placed on said support surface of said adsorption platform; and
    a controller arranged to control operations of said adsorption platform, said moving device and said detection device, wherein said controller:
    controls said moving device to place said pressing member on said printed circuit board such that the entire upper surface of said printed circuit board is pressed by said pressing surface while said printed circuit board is placed on said support surface of said adsorption platform, which is uncharged, and while said printed circuit board is not adsorbed on said support surface;
    after said pressing member is placed on said printed circuit board, switches said support surface of said adsorption platform to the charged state while said printed circuit board and said pressing member are placed on said support surface to cause said printed circuit board to be adsorbed on said support surface by an electrostatic force;

after said printed circuit board is adsorbed on said support surface, controls said moving device to remove said pressing member placed on said printed circuit board in said charged state of said support surface; and after said pressing member is removed, controls said detection device to perform automatic appearance inspection on said printed circuit board adsorbed on said support surface.

\* \* \* \* \*